United States Patent
Burgi et al.

[11] Patent Number: 5,235,409
[45] Date of Patent: Aug. 10, 1993

[54] OPTICAL DETECTION SYSTEM FOR CAPILLARY SEPARATION COLUMNS

[75] Inventors: Dean S. Burgi; John C. Helmer, both of Palo Alto; Ring-Ling Chien, San Jose, all of Calif.

[73] Assignee: Varian Associates, Inc., Palo Alto, Calif.

[21] Appl. No.: 744,563

[22] Filed: Aug. 13, 1991

[51] Int. Cl.⁵ .................. G01N 21/01; G01N 21/59; G01N 21/64

[52] U.S. Cl. ........................ 356/436; 356/72; 356/73; 356/244; 356/440; 359/737

[58] Field of Search ............ 356/436, 246, 244, 432, 356/335, 336, 337, 338, 73; 359/737, 775, 654

[56] References Cited

U.S. PATENT DOCUMENTS

| | | | |
|---|---|---|---|
| 3,512,889 | 5/1970 | Liston | 356/94 |
| 3,614,242 | 10/1971 | Hrdina et al. | 356/181 |
| 3,869,614 | 3/1975 | Munk | 250/365 |
| 3,966,323 | 6/1976 | Matsuoka et al. | 356/96 |
| 3,999,856 | 12/1976 | Unterlietner | 356/107 |
| 4,006,990 | 2/1977 | Munk | 356/246 |
| 4,192,614 | 3/1980 | deMey, II et al. | 356/410 |
| 4,375,163 | 3/1983 | Yang | 73/61.1 |
| 4,475,813 | 10/1984 | Munk | 356/73 |
| 4,558,953 | 12/1985 | Yamada | 356/409 |
| 4,747,687 | 5/1988 | Hoppe et al. | 356/246 |
| 4,795,262 | 1/1989 | Morris et al. | 356/436 |
| 4,826,660 | 5/1989 | Smith et al. | 422/68 |
| 5,037,199 | 8/1991 | Hlovsek | 356/246 |
| 5,074,658 | 12/1991 | Tavlarides et al. | 356/436 |

*Primary Examiner*—Vincent P. McGraw
*Assistant Examiner*—LaCharles Keesee

[57] ABSTRACT

On-column optical detection apparatus and method for use with capillary separation columns are shown. The apparatus and method minimize the adverse effects of light scattered from the walls of the column, thereby improving detection sensitivity and providing greater dynamic range. Light from a conventional source is focussed onto a column. Spatial filter means are positioned in front of the column to prevent at least some light from striking the column wall. Another spatial filter is positioned in front of a light collecting means which gathers light emanating from the column. In a specific embodiment, a unique monolens design is shown comprising collecting and focussing lens formed as an integral unit with a bore for a capillary column.

22 Claims, 3 Drawing Sheets

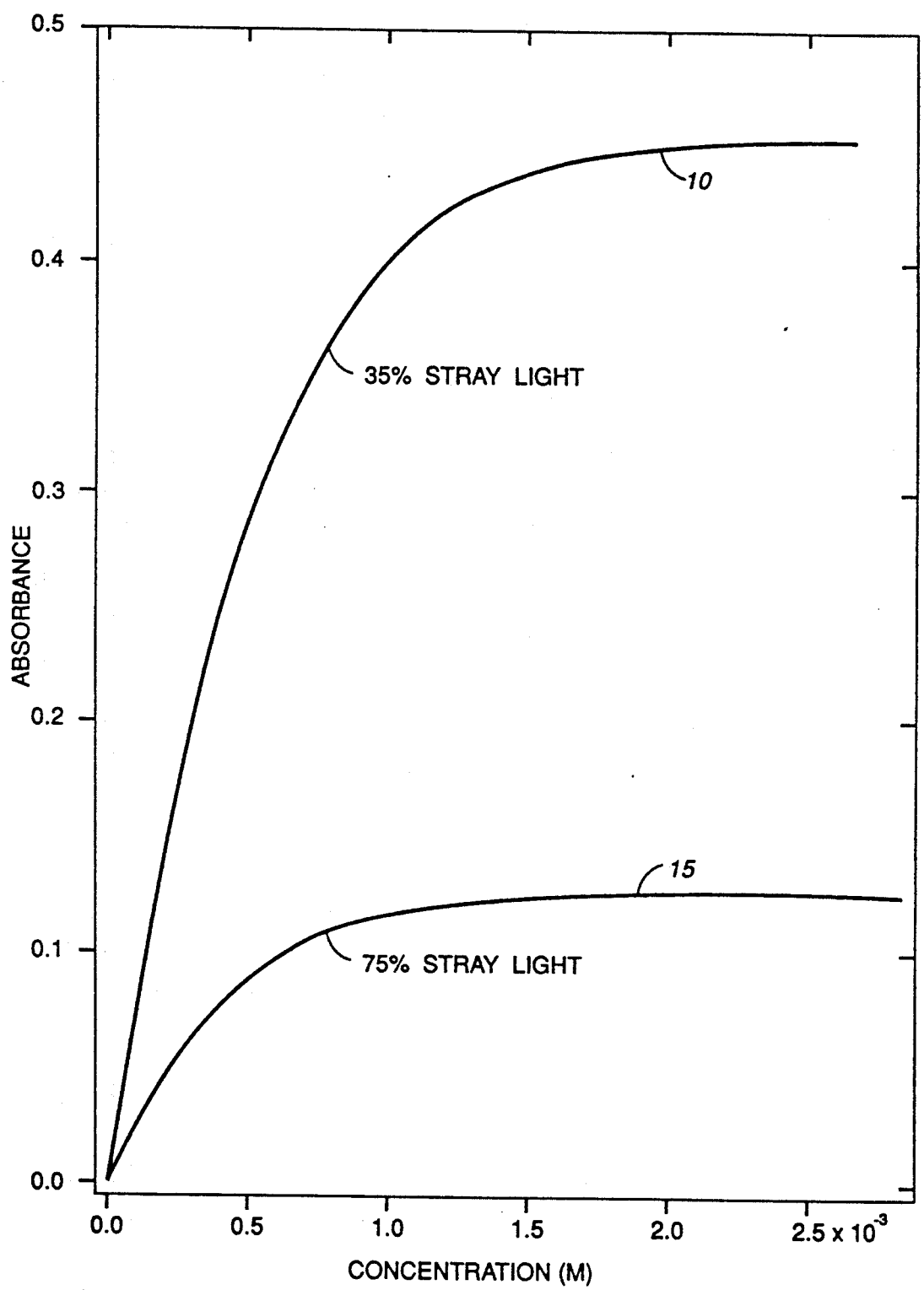
FIG._1

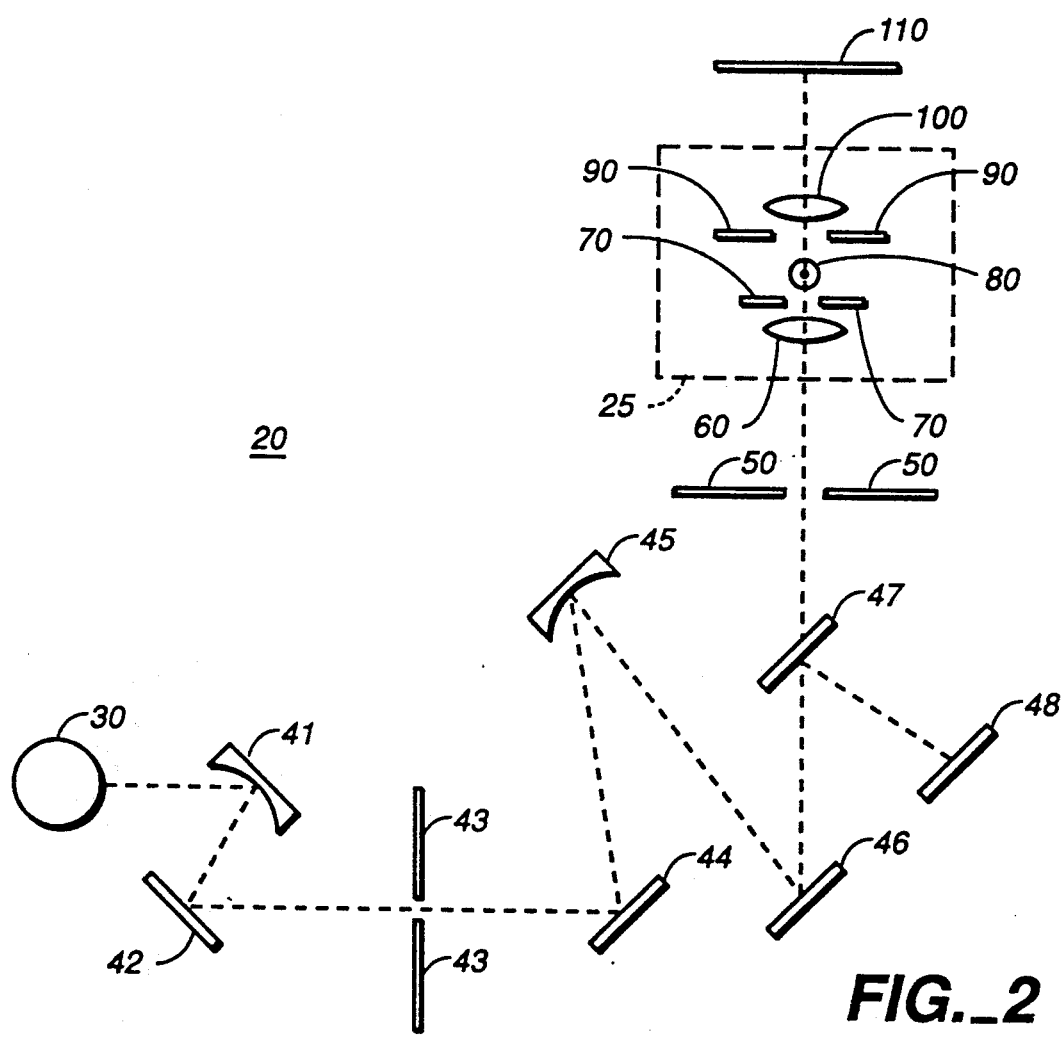
FIG._2

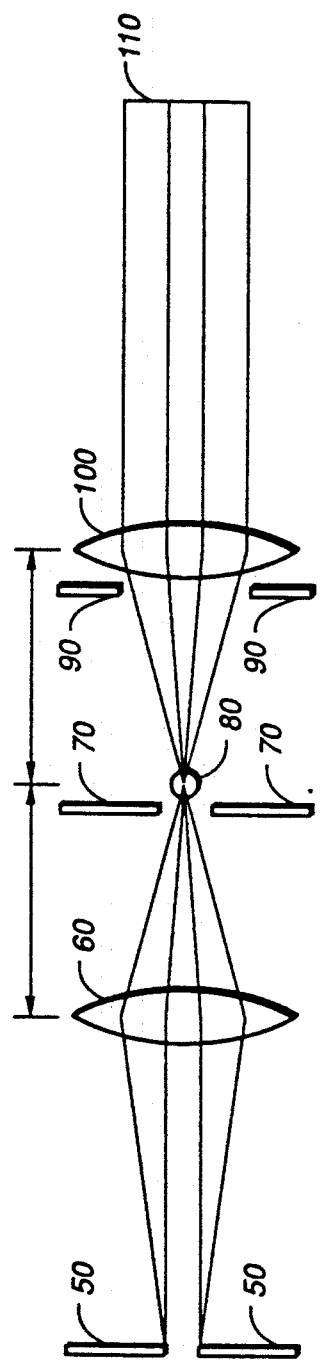
FIG._3
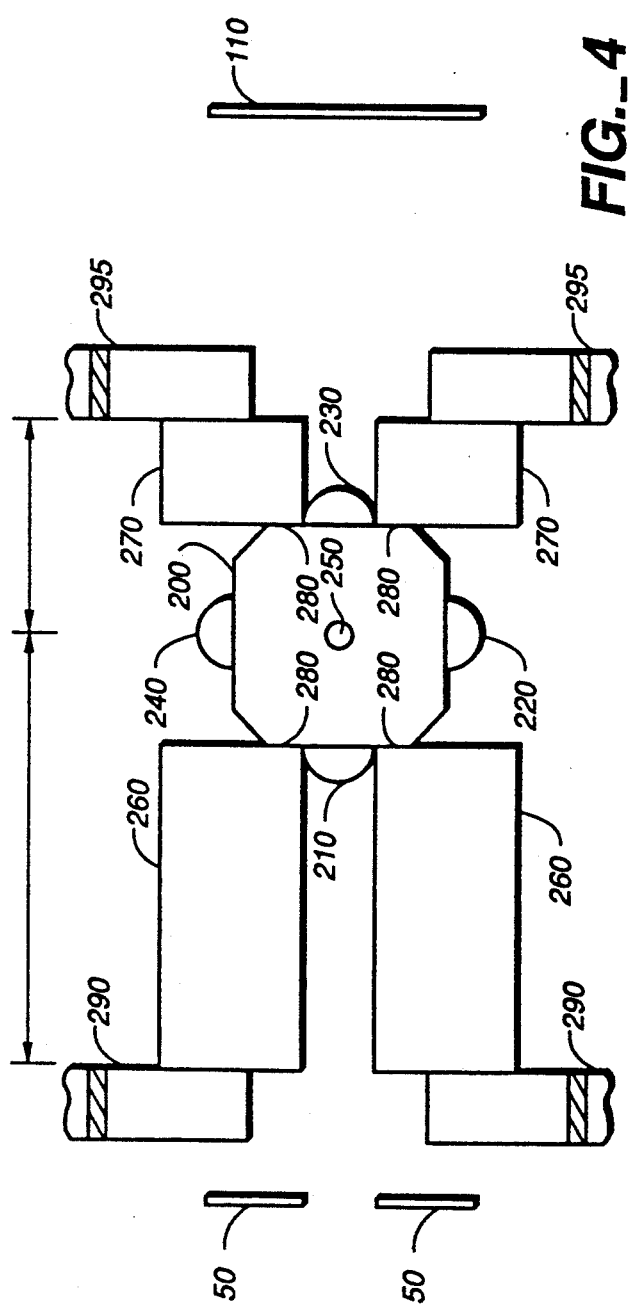
FIG._4

OPTICAL DETECTION SYSTEM FOR CAPILLARY SEPARATION COLUMNS

This invention relates to apparatus for measuring the optical properties of a sample contained in a capillary column, and is particularly useful in connection with measuring light absorbance of a fluid flowing through a capillary separation column.

BACKGROUND OF THE INVENTION

In chemical analysis it is often useful to measure one or more of the optical properties of an unknown sample. Such techniques, particularly when used in combination with other techniques, can provide qualitative and quantitative information about an unknown sample. Before optical measurements are made, an analyst may first use a separation technique to separate a sample into its constituents. Well known separation techniques include gas chromatography (GC), high performance liquid chromatography (HPLC), supercritical fluid chromatography (SFC) and capillary electrophoresis (CE). In systems employing these techniques a sample mixture is forced to flow through a separation column borne by a mobile phase. Different compounds in the sample move through the separation column at different speeds reaching the end of the column at different times. The elution of a sample component is commonly referred to as a "peak".

A variety of detection techniques and devices are available for qualitatively and quantitatively measuring a peak eluting from the end of a separation column. When using modern high resolution capillary separation techniques, a peak may consist of a very small mass of material which may elute over a relatively short time duration.

Various optical detection methods are in widespread use in HPLC, SFC and CE. Perhaps the most commonly used optical detection technique is absorbance detection wherein the optical absorbance of the sample flowing from the separation column is continuously measured. Fluorescence detection is another very commonly used technique. By measuring changes in the optical absorbance or fluorescence from background levels, qualitative and quantitative information about the sample may be obtained.

Generally, optical detection techniques used in connection with separation columns may be divided into two categories: those in which detection is performed "on-column" and those in which detection is performed using a flow-cell. On-column measurements are made by observing the properties of the sample near the end of the separation column but while the peak is still in the column. Flow-cells involve use of specially designed volumes for containing the flowing sample after it has eluted from the separation column. An example of a flow cell design for use in a liquid chromatography is shown in U.S. Pat. No. 4,006,990. Flow-cells can be designed to provide advantageous optical properties to enhance detection, but inherently add dead volume and cause fluid turbulence resulting in undesired peak broadening. On the other hand, on-column detection, while not suffering from the peak broadening problems associated with flow cells, does not offer very good optical properties.

The trend in separation science has been towards techniques capable of analyzing ever smaller samples. In the field of HPLC, this has resulted in the increased use of "microbore" or capillary columns. This trend has also led to increased use of SFC and CE, which are also performed using capillary columns. In systems using capillary columns sample volumes can be quite small. For example, to maintain high efficiency in CE, a sample plug must be less than 1 mm in length. Thus, when one uses a column having an inner diameter (ID) of 75 $\mu$m, the detection volume is on the order of 4 nL. The small size of capillary columns and of the sample volumes associated with capillary columns exacerbates the problems associated with using flow cells. As a result, on-column detection has been the preferred method for use with capillary separation columns. A basic design for on-column detection in capillary column HPLC is shown in U.S. Pat. No. 4,375,163. This patent also contains a more thorough discussion of the limitations of flow cells when dealing with very small sample volumes.

On-column detection techniques have the disadvantage, described above, of not offering good optical properties. A major problem with on-column optical detection in connection with capillary columns is due to light which is scattered and thereafter interferes with detection. A beam of light incident on a column will interact not only with the fluid within the column but also with the surrounding glass wall. A typical capillary column may have, for example, an outer diameter of 375 $\mu$m and an inner diameter of only 75 $\mu$m. Thus, a cross section of such a column has a 75 $\mu$m bore surrounded by two walls twice (150 $\mu$m) as wide. If light is evenly incident on the entire column, the majority will interact with the column walls rather than the sample. Scattered light will not only cause non-linearity in detector response at high absorption, it will also cause a reduction from the true absorption at low absorption.

Accordingly, it is an object of the present invention to provide an improved on-column optical detection method and apparatus for use with capillary separation columns.

Another object of the present invention is to provide a method and apparatus which minimizes light scatter in an on-column optical detection system.

Yet another object of the present invention is to provide a method and apparatus which minimizes the adverse effects of scattered light in an on-column optical detection system employing a capillary column.

Still a further object of the present invention is to provide a unique lens design which achieves the foregoing objects.

SUMMARY OF THE INVENTION

These and other objects that will be apparent to those skilled in the art are realized in the present invention comprising a light source for illuminating sample flowing through a capillary separation column, means for focussing the light onto the capillary column, means for masking said focussed light and thereby at least partially preventing it from striking the walls of the column, means for collecting light emanating from said column, spatial filter means for masking said light collecting means, thereby further reducing the effects of scattered light, and photodetector means for measuring light transmitted by said light collecting means. In the preferred embodiment said light focussing means and said light collecting means comprise a set of matched lenses equidistant from the capillary column, each lens being removed from said column a distance approximately equal to the focal length of the lens. In a specific implementation of the present invention, these lenses are formed as part of an integral "monolens" having at least two hemispherical portions and a central bore wherein the capillary column is positioned.

BRIEF DESCRIPTION OF THE DRAWINGS

FIG. 1 is plot of two curves showing the effect of scattered light on absorbance for two different levels of stray light.

FIG. 2 is a schematic diagram of an overall detection system according to the present invention in an absorbance detector.

FIG. 3 is a schematic diagram of an embodiment of the present invention also shown being used in an absorbance detection mode.

FIG. 4 is a plan view of an embodiment of the present invention using a novel monolens design.

DETAILED DESCRIPTION OF THE INVENTION

Under Beer's law $A = abc$, where A is the amount of light absorbed by a sample, a is the molar absorptivity of the sample, b is the path length of the light as it travels through the sample, and c is the concentration. The value of a, i.e., the molar absorptivity, is constant for each sample compound. Since the path length will vary across different portions of a cylindrical volume, such as a capillary column, it is necessary to integrate over the volume to obtain the total transmitted light. It can be shown that Beer's law for a cylinder can be expressed as $A = \pi/4 \, abc$, where b is the diameter of the column. In a system with a large amount of scattered or stray light, deviations from Beer's law will occur. The deviation will result in a measured absorbance $A'$ which differs from the true absorbance A. The measured absorbance is defined as:

$$A' = -\log \frac{I'}{I_0'} = -\log \frac{I + I_S}{I_0 + I_S}$$

where:

$I_0$ is the light incident on the sample region;
$I_S$ is the stray light intensity;
$I$ is the light transmitted from the sample region;
$I_0' = I_0 + I_S$ is the total incident light intensity; and
$I' = I + I_S$ is the total transmitted light intensity.

Substituting the true absorbance $A = -\log(I/I_0)$ into Eq. 1 we obtain a relation between the measured and the true absorption as follows:

$$A' = -\log \frac{10^{-A} + \frac{I_S}{I_0}}{1 + \frac{I_S}{I_0}}$$

At low absorption, where $A \ll 1$, this can be reduced as follows:

$$A' = -\log \frac{A}{1 + \frac{I_S}{I_0}}$$

Thus, stray light will cause a constant depression from the true absorbance, and thus stray light becomes a limiting factor in determining the detection level, i.e., the minimum amount of material that can be sensed.

At high absorption, where $A \gg 1$, Eq. 2 can be reduced as follows:

$$A' = -\log \frac{\frac{I_S}{I_0}}{1 + \frac{I_S}{I_0}}$$

Thus, the stray light becomes the limiting factor for the absorbance that can be measured. Accordingly, stray light affects the overall dynamic range of the detector at both ends, i.e., at high and at low absorption levels.

FIG. 1 is a plot of Eq. 4, based on theoretical calculations, assuming the presence of 35% (curve 10) and 75% (curve 15) stray light. The pronounced effects of stray light can be clearly seen as the curves approach limiting absorbencies of 0.45 and 0.12 respectively. Data collected in connection with the development of the present invention shows that the amount of stray or scattered light present in a capillary on-column optical detection system of the prior art can easily be in the range of 35-75%.

While the adverse effects of stray light have been shown in connection with optical absorbance, it will be appreciated by those skilled in the art that similar adverse effects will occur in other systems, e.g., in a fluorescence detector. Accordingly, while the present invention is, for convenience, described primarily in connection with absorption detection, it is not intended to be so limited, and it will be clear to those skilled in the art that the benefits herein described will be applicable to other optical detection apparatus.

The present invention is directed to apparatus and methods for minimizing the effects of stray light so as to provide greater dynamic range and improved linearity of detector response. The reduction of stray light is accomplished using a combination of techniques each of which reduces stray light in the system.

An overall absorbance detector 20 in accordance with a preferred embodiment of the present invention is shown schematically in FIG. 2 to which we now turn. A lamp 30 provides light for use in the detector. This light is processed in a known manner by optical elements 41-47. In the embodiment shown, one of these optical elements, grating 46, is used to provide monochromatic light. It should be understood that as used herein the term "light" is intended to include radiation in the ultraviolet (UV) portion of the electromagnetic spectrum, in addition to "visible" and infrared light. UV light is very commonly used in absorbance and fluorescence detection in HPLC, CE and SFC.

Light from grating 46 passes through exit slit 50 and follows a path through focussing lens 60, slit 70, capillary column 80, spatial filter 90, and collecting lens 100 according to the present invention and as described below in greater detail in connection with FIG. 3. A portion of the unfiltered, unabsorbed light which exits collecting lens 100 reaches photodiode 110 where it is detected using known current measurement techniques. Except for the modifications within dashed line 25 which are shown in greater detail in FIG. 3 and described below, an embodiment of system 20 used by the inventors is a modified version of a commercially available UV detector design which can be purchased as Varian Model No. 2550. This commercial detector is designed for use with large-bore HPLC and requires modification for use with capillary columns. While an embodiment of the present invention has been built using the Varian apparatus, it should be apparent that alternative designs and techniques are widely available. In particular, everything up to exit slit 50 can be replaced by a number of known designs and techniques for producing monochromatic light. Moreover, in some applications monochromatic light is unneeded and may not be desired.

Turning now to FIG. 3, ray tracings are shown in connection with the apparatus of the present invention to illustrate the methods employed to minimize the stray light reaching photodiode 110. Monochromatic light passing through exit slit 50 is shown having a slight amount of divergence. In the embodiment using the aforementioned commercial system, the angle of divergence was approximately 8°. This light is captured by lens 60 and focussed onto capillary column 80. Capillary column 80 is made of fused silica which is optically transparent to light radiation at the wavelengths of interest and, in particular, to UV light. Any coating on the column is removed in the area where light is to be focussed, as described in the aforementioned U.S. Pat. No. 4,375,163.

Using a commercially available lens, it is possible to focus light from exit slit 50 down to a spot slightly less than 1 mm in diameter. As noted above, in CE a sample plug be approximately 1 mm in length, and in capillary column HPLC a sample plug may be even longer. Thus, if a focal spot were significantly smaller than 1 mm less of the sample would be illuminated, to the detriment of the efficiency of the system. However, a 1 mm focal spot is still much larger than the outer diameter of the typical capillary column used for separation. Accordingly, slit 70 is positioned in front of column 80 to block or mask light which would otherwise strike the column walls and be scattered. When using a column with an inner diameter of 75 $\mu$m and an outer diameter of 375 $\mu$m, it has been found that a 100 $\mu$m slit greatly reduces the stray light without adversely affecting illumination of the sample.

In theory, it would appear that the width of the slit should be approximately the same size as the inner diameter of the column to minimize the amount of light striking a portion of the column wall that is not in front of the column bore. However, when working with the very small dimensions involved, the miniature size of the slit will make the task of attaining and maintaining the nearly perfect optical alignment which is required very difficult. These alignment problems are mitigated by the use of a 100 $\mu$m slit. If a slit smaller than the diameter of the column, i.e., less than 75 $\mu$m were used, or if alignment is not accurate, the illumination of the sample would be reduced, to the detriment of the signal-to-noise ratio of the system.

After passing through slit 70 and column 80, the remaining light is incident on collecting lens 100. In the preferred embodiment, lenses 60 and 100 are a matched pair and are coaxially aligned. In one embodiment, two commercially available 6 mm diameter quartz lenses with a 5 mm focal length were used. Moreover, as is explained in greater detail below, it has been found that by placing lens 100 approximately the same distance from the column as lens 60, the effects of stray light are further reduced. It should be noted that, in this configuration, the distance between the column and either lens is approximately the focal length of the lens. Thus, light exiting collecting lens 100 will have approximately the same angle of divergence as the light reaching the lens 60 in accordance with well known principles of optics.

A mask or spatial filter 90 is placed in front of lens 100, i.e., between column 80 and the lens. In the above described embodiment, spatial filter 90 had an aperture diameter of 2 mm and thus blocks a significant portion of the periphery of the lens. Use of a spatial filter in front of lens 100 was found to further reduce the amount of stray light reaching photodiode 110.

A series of experiments were conducted to evaluate the various techniques used to minimize stray light. The results of the experiments are shown below:

TABLE 1

| Optical Design | Detection Limit - Uracil (moles/Liter) |
| --- | --- |
| A) Slit only | $7.0 \times 10^{-6}$ |
| B) A & Focussing Lens | $3.3 \times 10^{-6}$ |
| C) B & Collecting Lens @ 9 mm, & mask | $2.5 \times 10^{-6}$ |
| D) B & Collecting Lens @ 5 mm, no mask | $5.0 \times 10^{-6}$ |
| E) D & mask | $9.1 \times 10^{-7}$ |

Optical design C is similar to that shown in FIG. 3, however, the collecting lens is positioned farther away from the column, i.e., 9 mm, with the result that the collected light is focussed onto the photodiode. Comparing design C with the design of the present invention, i.e., design E, it should be noted that placing the collecting lens at a distance approximately equal to its focal length, so that the light from the column is slightly divergent, improves sensitivity by a factor of almost three. Likewise, use of a mask improves sensitivity by a factor greater than five over a comparable maskless design, i.e., design D.

While data suggest that, at least in the designs tested, use of a spatial filter or mask in front of the collecting lens provides a greater improvement of detection limit than positioning of the collecting lens, proper positioning of the collecting lens can be quite significant.

The primary source of stray light emanating from the column is, as noted above, from the column walls. Use of a ray tracing programs has shown that this light will mostly be at the periphery of the beam passing through the sample in the column, and will stay at the periphery. Placement of a properly sized spatial filter or mask will prevent this peripheral light from reaching the photodiode. It is believed that even more dramatic improvements in the detection limit can be obtained be carefully sizing and configuring the spatial filter.

For example, the mask need not have a circular aperture since the sample is not circular. Rather the sample is closer to being cylindrical. Thus, a rectangular or elliptical aperture is likely to be an improvement over the design tested.

Moreover, while the preferred embodiment is shown wherein the spatial filter is positioned in front of the collecting lens, in an alternate embodiment, the spatial filter is placed in front of the photodiode. Again, the purpose of this is to block the periphery of the light beam where most of the scattered light is present. However, in the design of the present invention the photodiode is, effectively, self-masking due to the placement of collecting lens 100.

In accordance with the preferred embodiment of the present invention collecting lens 100 is positioned a distance approximately equal to its focal length from the column. As explained above, as a result of this placement, light passing through the lens is substantially collimated or even slightly divergent. Assuming that the photodiode is properly sized, light at the periphery of the beam from lens 100 will miss the photodiode. Again, the primary component of the peripheral light is light scattered from the column walls. In comparison, in design C, where the collecting lens is positioned so as to produce a converging beam, the peripheral scattered light is focussed on the photodiode.

This self-masking phenomenon explains the apparently incongruous result shown in Table 1, where the detection limit of design B, i.e., a slit and a focussing lens, (but no collecting lens), is better than that of design D, i.e., a slit, a focussing lens and a collecting lens without a mask. In design B, light coming from the column is highly divergent, and thus almost none of the scattered light at the periphery of the beam will land on the photodiode. By properly sizing and positioning the photodiode, it is believed to be possible to rely entirely on this self-masking effect, eliminating the need for a collecting lens with a spatial filter in front of it.

The concentration detection limits of uracil obtained in accordance with the present invention correspond to a mass detection limit of 0.01 pg. This is a factor of five improvement over the detection limit reported for a commercially available UV absorbance detector. Similar tests using anthracene as a sample, resulted in a concentration detection limit of $5.4 \times 10^{-8}$M, which translates to a mass detection limit of 38 fg. This is a factor of five improvement over the maskless two lens design (i.e., design E), and is an order of magnitude better than a commercially available spherical ball detector. Anthracene was used because of its large molar absorptivity and, as a result, has become a standard in the chromatography field for comparing UV detectors. The detection limit obtained for anthracene is close to the theoretically calculated value of the system detection limit based on the fact that such a system is photon shot noise limited.

In another implementation of the present invention, a "monolens" was constructed in accordance with the design of FIG. 4. The monolens comprises a central quartz body portion 200 with four quartz hemispherical lobes 210, 220, 230 and 240, respectively, which serve as lenses. Hemispherical lobes 210 and 230 are coaxially aligned, as are hemispherical lobes 220 and 240, with all four having their axes lying on the same plane. In one embodiment, the quartz hemispherical attachments are glued to body portion 200 using glue which is transparent to the light frequencies of interest. Alternately, the body and hemispherical lobes can be machined out of a single piece of quartz so as to form an integral unit. Although four hemispherical lobes are shown, in most applications it will only be necessary to provide two such lobes. The monolens of FIG. 4 was designed in order to allow both absorbance detection and fluorescence detection. For fluorescence detection it is desirable to position the collecting lens at right angles to the focussing lens to further minimize the effects of stray light.

At the center of body portion 200 and equidistant from the hemispherical lobes is a bore 250 barely wide enough to accommodate capillary column 80. In one design, the central bore was specified to be 0.5 mm in diameter. This allows the monolens to be used for on-column detection. Accordingly, the column is inserted into the bore where it is surrounded by the monolens. While the bore should be close in diameter to the outer diameter of the capillary column, it is inevitable that there will be gaps between the column and the monolens. To minimize refraction problems which could arise as the light travels through these gaps, the space between the monolens and the column may be filled with a fluid having an index of refraction nearly the same as quartz.

The body portion and hemispherical lobes of the monolens are dimensioned such that light incident on one of the hemispherical lobes is focussed at a point at the center of column 80, i.e., the center of bore 250. With this design the focal spot can be substantially smaller than the 1 mm focal spot described above in respect to a commercially available lens. If the focal spot is made small enough, for example, 75-100 μm, and if the design is accurately made, there is no longer a need for a slit to partially block light from striking the column walls. Light will not strike the periphery of the column walls by virtue of being tightly focussed. In one embodiment, the focal spot was calculated to be 83 μm, or just slightly larger than the inner diameter of the capillary column.

When using the monolens design it is not practical to place a slit in front of the column, nor is it practical to place a spatial filter in front of the collecting lens. Rather, as shown in FIG. 4, a spatial filter 260 is placed in front of focussing lens 210 and another spatial filter 270 is places behind collecting lens 230. In the embodiment shown in FIG. 4, spatial filters 260 and 270 also serve to keep the monolens properly positioned by holding it at shoulders 280 adjacent the hemispherical lobes. Spatial filters 260 and 270 are, in turn, held in position by lens holders 290 and 295 respectively.

Although positioned differently than in the design of FIG. 3, spatial filters 260 and 270 nonetheless serve to reduce the amount of light scatter in the optical detector. As noted before, light from exit slit 50 will be slightly divergent. The amount of divergence is 8° for the aforementioned Varian 2550 detector. Spatial filter 260 blocks some of the diverging light, and further blocks other stray light which may be present in the system. Likewise, light transmitted by collecting lens 230 will be slightly divergent, with the scattered light being mostly at the periphery of the transmitted beam. Spatial filter 270 helps block the diverging peripheral portion of the beam.

Static tests were performed using the monolens design, with uracil again being used as the absorbing compound. A detection limit of $9.3 \times 10^{-7}$M was obtained, which is virtually the same detection limit as was obtained using the embodiment of FIG. 3. Again, it is believed that this is subject to improvement as the dimensions of the optical elements and filters are maximized. Nonetheless, the detection limits reported show a substantial improvement over the prior art.

Although the present invention has been described in detail with reference to the embodiments shown in the drawings, it is not intended that the invention be restricted to such embodiments. It will be apparent to those skilled in the art that various modifications and departures from the foregoing description and drawings may be made without departing from the scope or spirit of the invention. Therefore, it is intended that the invention be limited only by the following claims.

What is claimed is:

1. An optical detection system for use with a capillary column, comprising:

illumination means for providing a beam of light;

light focussing means for focussing said light beam onto a portion of said column wherein separated sample flows, said focussed beam being generally perpendicular to the axis of said column;

slit means adjacent to said column, and positioned in the light path between said focussing means and said column, to at least partially block light from striking the sides of said column;

light collecting means for collecting light passing through said column and producing a beam;

spatial filter means adjacent said light collecting means and positioned in the light path between said capillary column and said light collecting means for preventing light from striking the periphery of said light collecting means; and, photodetector means positioned to receive at least a portion of the light from said light collecting means.

2. The optical detection system of claim 1 wherein said light collecting means produces a beam which does not converge.

3. The optical detection system of claim 1 wherein said light focussing means comprises a lens.

4. The optical detection system of claim 1 wherein said light collecting means comprises a lens.

5. The optical detection system of claim 1 wherein said light focussing means and said light collecting means comprise a set of coaxially aligned matched lenses placed equidistant from the column.

6. The optical detection system of claim 5 wherein said lenses are spaced a distance from the column equal to the focal length of said lenses.

7. The optical detection system of claim 1 wherein said photodetector means comprises a photodiode having a planar surface.

8. The optical detection system of claim 7 wherein said photodiode is configured and positioned such that light in the peripheral portion of the beam emanating from the collecting lens does not strike the photodiode surface.

9. The optical detection system of claim 7 further comprising second spatial filter means adjacent said photodiode planar surface.

10. The optical detection system of claim 1 wherein the width of said slit means is no greater than approximately 1.5 times the inner diameter of said column.

11. An detection system for measuring the optical properties of a sample flowing through a cylindrical capillary column, comprising:

a light source for providing light including at least one light frequency of interest;

a first lens for focussing said light within an interior volume of said column, said first lens being located a distance from said column approximately equal to its focal length;

a slit adjacent to said column having a width greater than the inner diameter of said column but smaller than the outer diameter of said column;

a second lens, substantially the same as said first lens, for collecting light passing through said column, said second lens being coaxially aligned with and equidistant from the column as is said first lens;

a spatial filter adjacent to said second lens, and positioned between said column and said second lens, said spatial filter being configured to block at least some of the light at the periphery of the light beam emanating from the column from reaching said second lens; and, photodiode means for measuring the light transmitted by said second lens.

12. The detection system of claim 11 wherein said light source produces monochromatic light.

13. A monolens for use in an optical detection system, comprising:

a body portion having a central bore, said bore having a diameter slightly greater than the diameter of a capillary column;

a first hemispherical portion for focussing light, said first hemispherical portion being located at the periphery of said body portion and positioned such that the axis of said first hemispherical portion is perpendicular to the axis of said bore;

a second hemispherical portion for collecting light, said second hemispherical portion being located opposite said first hemispherical portion at the periphery of said body portion and equidistant from said bore, said second hemispherical portion being coaxially positioned with said first hemispherical portion.

14. The monolens of claim 13 further comprising shoulders at least partially surrounding said hemispherical portions.

15. The monolens of claim 13 further comprising a third hemispherical portion for collecting light, said third hemispherical portion being located at the periphery of said body portion and positioned such that the axis of said third hemispherical portion is perpendicular to the axis of said bore and is also perpendicular to the axis of said first and second hemispherical portions.

16. The monolens of claim 13 wherein said hemispherical portions are separately formed and thereafter attached to said body portion.

17. The monolens of claim 13 wherein said hemispherical portions and body portion are formed from a unitary block.

18. A method of optical detection of a sample in a capillary separation column comprising the steps of:

providing a beam of light;

focussing said beam of light onto said capillary column;

at least partially blocking the beam from striking the walls of the column;

spatially filtering the light beam emanating from the capillary column so as to block light at the periphery of said light beam;

collecting the remaining unfiltered light emanating from the column using a light collecting means, which produces a collected beam;

positioning a photodiode in the path of collected beam such that only the light in the central portion of said beam strikes said photodiode.

19. The method of claim 18 wherein the step of collecting comprises using a light collecting means which produces a non-convergent collected beam.

20. The method of claim 18 wherein the step of focussing the light beam onto the column comprises the placing a lens in the path of said light beam at a position relative to the column approximately equal to the focal length of the lens.

21. The method of claim 18 wherein the step of collecting the light beam emanating from the column comprises the placing a lens in the path of said light beam at a position relative to the column approximately equal to the focal length of the lens.

22. The method of claim 18 wherein said focussing means and said light collecting means comprise a matched pair of lenses.

* * * * *